(12) United States Patent
Ferrante et al.

(10) Patent No.: US 12,249,144 B2
(45) Date of Patent: Mar. 11, 2025

(54) MONITORING SURFACE CLEANING OF MEDICAL SURFACES USING VIDEO STREAMING

(71) Applicant: Digital Diagnostics Inc., Coralville, IA (US)

(72) Inventors: Joseph Ferrante, Cambridge, MA (US); Kelsey Gross, Seattle, WA (US); Elliot Swart, Phoenix, AZ (US)

(73) Assignee: Digital Diagnostics Inc., Coralville, IA (US)

( * ) Notice: Subject to any disclaimer, the term of this patent is extended or adjusted under 35 U.S.C. 154(b) by 448 days.

(21) Appl. No.: 17/621,570

(22) PCT Filed: Jun. 26, 2020

(86) PCT No.: PCT/US2020/039918
§ 371 (c)(1),
(2) Date: Dec. 21, 2021

(87) PCT Pub. No.: WO2020/264367
PCT Pub. Date: Dec. 30, 2020

(65) Prior Publication Data
US 2022/0358761 A1    Nov. 10, 2022

Related U.S. Application Data

(60) Provisional application No. 62/868,243, filed on Jun. 28, 2019.

(51) Int. Cl.
*G06V 20/40* (2022.01)
*A61L 2/24* (2006.01)
(Continued)

(52) U.S. Cl.
CPC ............... *G06V 20/41* (2022.01); *A61L 2/24* (2013.01); *A61L 2/28* (2013.01); *G06T 7/70* (2017.01);
(Continued)

(58) Field of Classification Search
CPC .... G06V 20/41; G06V 10/764; G06V 10/774; G06V 10/82; G06V 20/40; G06V 20/52;
(Continued)

(56) References Cited

U.S. PATENT DOCUMENTS

2012/0073604 A1    3/2012  Barnhill et al.
2012/0116803 A1*   5/2012  Reid ................. G16H 40/20
                                                  705/2

(Continued)

FOREIGN PATENT DOCUMENTS

CN    106489101 A    3/2017
CN    106687960 A    5/2017
(Continued)

OTHER PUBLICATIONS

PCT International Search Report and Written Opinion, International Application No. PCT/US2020/039918, dated Sep. 14, 2020, 11 Pages.
(Continued)

*Primary Examiner* — Edward F Urban
*Assistant Examiner* — Wassim Mahrouka
(74) *Attorney, Agent, or Firm* — Fenwick & West LLP

(57) ABSTRACT

A cleaning wizard monitors and provides feedback for cleaning of medical equipment to ensure that cleaning is performed based on best practices. The cleaning wizard receives a video stream comprising an item of medical equipment and inputs a first set of video frames from the video stream into a first machine learning model. The first machine learning model is trained to output whether the first
(Continued)

set of video frames corresponds to activity that initiates a cleaning protocol for the item of medical equipment. Responsive to the cleaning protocol being initiated, the cleaning wizard inputs a second set of video frames into a second machine learning model trained to output whether the second set of frames meets criteria of the cleaning protocol. Responsive to all criteria of the cleaning protocol being met, the cleaning wizard transmits a notification to an operator that the cleaning protocol is complete.

18 Claims, 5 Drawing Sheets

(51) Int. Cl.
*A61L 2/28* (2006.01)
*G06T 7/70* (2017.01)
*G06V 10/764* (2022.01)
*G16H 40/20* (2018.01)
*G16H 40/67* (2018.01)

(52) U.S. Cl.
CPC ........... *G06V 10/764* (2022.01); *G16H 40/20* (2018.01); *G16H 40/67* (2018.01); *A61L 2202/17* (2013.01); *A61L 2202/24* (2013.01); *A61L 2202/25* (2013.01); *G06T 2207/10016* (2013.01); *G06T 2207/20081* (2013.01)

(58) Field of Classification Search
CPC .......... A61L 2/24; A61L 2/28; A61L 2202/17; A61L 2202/24; A61L 2202/25; G06T 7/70; G06T 2207/10016; G06T 2207/20081; G16H 40/20; G16H 40/67; B08B 13/00; A61B 90/70; A61B 2562/245; G08B 21/245; G06N 3/044; G06N 3/0464; G06N 3/08; G06N 20/00
See application file for complete search history.

(56) References Cited

U.S. PATENT DOCUMENTS

| | | | | |
|---|---|---|---|---|
| 2013/0279779 A1* | 10/2013 | Darrow | .................. | A61B 5/055 382/131 |
| 2014/0241571 A1* | 8/2014 | Bilet | ..................... | G06T 7/0004 382/103 |
| 2015/0109193 A1 | 4/2015 | Sly et al. | | |
| 2016/0360165 A1* | 12/2016 | Hurley | ................... | G16H 40/67 |
| 2018/0169286 A1 | 6/2018 | Henniges et al. | | |
| 2018/0247711 A1 | 8/2018 | Terry | | |
| 2018/0344309 A1 | 12/2018 | Nawana et al. | | |
| 2018/0357886 A1* | 12/2018 | Tavori | .................... | G16H 40/20 |
| 2019/0147220 A1* | 5/2019 | McCormac | ........ | G06V 10/7715 382/103 |
| 2019/0239716 A1* | 8/2019 | Choi | .................... | A47L 15/4295 |
| 2019/0331701 A1* | 10/2019 | Polley | ................ | G01N 35/0099 |

FOREIGN PATENT DOCUMENTS

| | | |
|---|---|---|
| CN | 107122581 A | 9/2017 |
| CN | 108154098 A | 6/2018 |
| JP | 2009-291308 A | 12/2009 |
| JP | 2019-79144 A | 5/2019 |
| WO | WO 2007/129289 A1 | 11/2007 |
| WO | WO 2017/094016 A1 | 6/2017 |
| WO | WO 2019/054949 A1 | 3/2019 |
| WO | WO 2019/109242 A1 | 6/2019 |

OTHER PUBLICATIONS

Armellino et al. Remote Video Auditing to Verify OR Cleaning: A Quality Improvement Project. Dec. 14, 2018 (Dec. 14, 2018). [retrieved on Aug. 27, 2020]. Retrieved from the Internet:<URL: http://arrowsight-media-public.s3.amazonaws.com/AORN+Northwell+Study+on+OR_Cleaning+%26+SSIs+2018.pdf> pp. 634-642.
China National Intellectual Property Administration, Office Action, Chinese Patent Application No. 202080060434.4, Apr. 13, 2023, 9 pages.
Canadian Intellectual Property Office, Office Action, Canadian Patent Application No. 3,145,430, Jul. 5, 2023, 5 pages.
European Patent Office, Extended European Search Report and Written Opinion, European Patent Application No. 20831046.6, Jun. 15, 2023, 12 pages.
Japan Patent Office, Office Action, Japanese Patent Application No. 2021-576596, Jul. 24, 2024, 12 pages.

* cited by examiner

MONITORING SURFACE CLEANING OF MEDICAL SURFACES USING VIDEO STREAMING

CROSS REFERENCE TO RELATED APPLICATIONS

This application is a national phase of International Application No. PCT/US2020/039918, titled "Monitoring Surface Cleaning of Medical Surfaces Using Video Streaming," filed on Jun. 26, 2020, which claims the benefit of U.S. Provisional Application No. 62/868,243 filed on Jun. 28, 2019, the contents of both of which are hereby incorporated by reference herein in its entirety.

BACKGROUND

This disclosure relates generally to using a camera in conjunction with machine learning to monitoring cleaning of surfaces, and more particularly to using video streaming to monitor and provide feedback of adherence to protocol for cleaning of medical surfaces.

In healthcare, it is vital for medical equipment to be cleaned properly in order to control and reduce the spread of infections among patients. For example, small medical equipment that makes contact with patients' skin, such as stethoscopes and thermometers, may contribute to the spread of infection. As a particular example, stethoscopes, most significantly the diaphragm, have been shown to be almost 100% contaminated by potential pathogens and skin flora, which are commonly acquired from colonized or infected patients. It is widely understood and documented that the level of stethoscope contamination, even after a single physical examination, is comparable to the contamination of parts of a physician's dominant hand. Similar types of medical equipment that come into direct contact with patients' skin or membranes are at risk for this level of contamination as well.

Despite thorough documentation of contamination within healthcare environments, compliance to environmental cleaning standards and protocols vary, leading to outbreaks. Issues with compliance include failure to follow appropriate preparation, timing, and application of disinfectants, as specified by manufacturer instructions, and inconsistency in workflows, creating a lack of standardized protocols and adherence to best practices.

SUMMARY

The above and other issues are addressed by a cleaning wizard that monitors and provides feedback during cleaning of medical surfaces using video streaming. A video stream is captured by a camera and transmitted to the cleaning wizard. The camera may be mounted to or within the item of medical equipment, or may be externally positioned to capture a view of the item of medical equipment. Based on the video data, the cleaning wizard monitors cleaning protocols for the item of medical equipment and notifies one or more operators when a cleaning protocol requires attention, fails, or is complete based on best practices including CDC guidelines and manufacturer instructions.

In an embodiment, the cleaning wizard receives a video stream including frames depicting medical equipment. The cleaning wizard determines, based on the video stream, when a cleaning protocol for the item of medical equipment is initiated. In an embodiment, the cleaning wizard inputs the video stream data to a machine learning model to detect when cleaning is initiated. For example, the machine learning model is trained to output that a cleaning protocol is initiated when a wiping motion with a cloth is detected in the video stream moving across a surface of the item of medical equipment.

Responsive to a cleaning attempt being detected, the cleaning wizard may monitor the video stream to ensure that a cleaning agent is correctly applied to the surface of the item of medical equipment, and that the cleaning agent is applied sufficiently to meet manufacturer instructions. For example, many cleaning agents require that a surface is kept sufficiently wet for a length of time to fully clean the surface. In order to maintain the wetness of the surface, the operator may be notified and required to reapply the cleaning agent during the length of time. In an embodiment, the cleaning wizard inputs the video stream data to one or more machine learning models trained to output whether the video stream meets criteria of the cleaning protocol.

Where the cleaning wizard determines that the cleaning shown in the video stream is in danger of failing the criteria of the cleaning protocol, the cleaning wizard may notify an operator to perform corrective actions, such as applying cleaning agent to a missed surface area or reapplying cleaning agent to an area that is approaching insufficient wetness. Where the cleaning wizard determines that the cleaning shown in the video steam fails the criteria of the cleaning protocol, the cleaning wizard may notify an operator to restart a portion of, or the entirety of, the cleaning protocol. When the cleaning wizard determines that the cleaning shown in the video stream meets the criteria of the cleaning protocol, the cleaning wizard may notify the operator that the cleaning protocol has been completed.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Figure 1:
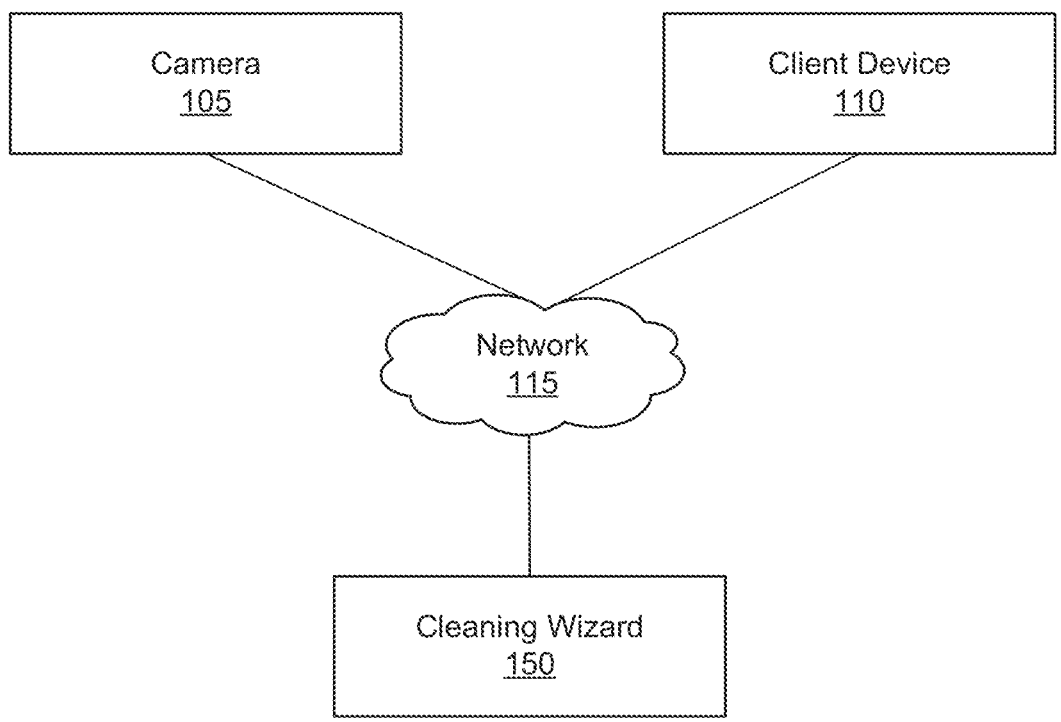
FIG. 1 is a block diagram of a system environment in which a cleaning wizard operates, in accordance with an embodiment.

FIG. 1 is a block diagram of a system environment 100 for a cleaning wizard 150. The system environment 100 shown by FIG. 1 comprises a camera 105, a client device 110, a network 115, and a cleaning wizard 150. In alternative configurations, different and/or additional components may be included in the system environment 100. For example, the system environment 100 may include one or more cameras 105 and one or more client devices 110.

The client devices 110 are one or more computing devices capable of receiving user input, displaying information to a viewing user, and transmitting and/or receiving data via the network 115. In one embodiment, a client device 110 is a conventional computer system, such as a desktop or laptop computer. Alternatively, a client device 110 may be a device having computer functionality, such as a personal digital assistant (PDA), a mobile telephone, a smartphone, or another suitable device. A client device 110 is configured to communicate via the network 115. In one embodiment, a client device 110 executes an application allowing a user of the client device 110 to interact with the cleaning wizard 150. For example, a client device 110 executes a browser application to enable interaction between the client device 110 and the online system 150 via the network 115. In another embodiment, a client device 110 interacts with the online system 150 through an application programming interface (API) running on a native operating system of the client device 110, such as IOS® or ANDROID™.

The client devices 110 are configured to communicate via the network 115, which may comprise any combination of local area and/or wide area networks, using both wired and/or wireless communication systems. In one embodiment, the network 115 uses standard communications technologies and/or protocols. For example, the network 115 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 115 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 115 may be represented using any suitable format, such as hypertext markup language (HTML) or extensible markup language (XML). In some embodiments, all or some of the communication links of the network 115 may be encrypted using any suitable technique or techniques.

One or more cameras 105 may be coupled to the network 115 for communicating with the cleaning wizard 150, which is further described below in conjunction with FIGS. 2A-2B and FIG. 3. A camera 105 captures a video stream comprising a continuous series of image frames and transmits the captured video stream to the cleaning wizard 150. In an embodiment, a camera 105 is a component of a client device 110, e.g., a camera on a laptop or desktop computer. In an embodiment, the camera 105 is internal to an item of medical equipment, e.g., built-in or mounted to or in an item of medical equipment (e.g., a lens of camera 105 is to be cleaned, the lens being the item of medical equipment). In another embodiment, the camera is external to the item of medical equipment, and may be positioned to capture a video stream including the item of medical equipment.

The cleaning wizard 150 receives video data from the one or more cameras 105 and monitors the video stream to determine when a cleaning protocol is initiated by an operator for an item of medical equipment. In an embodiment, initiation of a cleaning protocol is defined by an initial application of a cleaning agent to a surface of the item of medical equipment. A cleaning agent may include one or more liquids, sprays, towelettes, wipes, etc., that require an operator to leave the surface sufficiently wet for a length of time and/or perform certain additional interactions with the surface. Cleaning agents may be applied via wiping, spraying, rinsing, or other methods. When a cleaning protocol is initiated, the cleaning wizard 150 monitors a video stream for the cleaning attempt to ensure that the cleaning attempt meets all criteria of the cleaning protocol, including, for example, sufficient coverage of a surface of the item of medical equipment, sufficient wetness of a surface of the item of medical equipment, and a sufficient duration of time elapsed with the cleaning agent applied to a surface of the item of medical equipment. During the cleaning protocol, if the cleaning attempt is in danger of failing the criteria of the cleaning protocol, the cleaning wizard 150 transmits notifications to a client device 110 of the operator to correct deficiencies in the cleaning attempt. When all criteria of the cleaning protocol are met, the cleaning wizard transmits a notification to a client device 110 of the operator that the cleaning protocol is complete. Further details of activity of cleaning wizard 150 are described below with respect to FIGS. 2-5.

As shown in the example of FIG. 1, the cleaning wizard 150 is remotely hosted and is fully operated on the cloud, e.g., via a service provider such as AMAZON WEB SERVICES, MICROSOFT AZURE, or GOOGLE CLOUD PLATFORM. In another embodiment, some or all of the cleaning wizard 150 is implemented locally. For example, some or all of the cleaning wizard 150 is operated onboard one or more cameras 105 and/or one or more client devices 110.

Figure 2A:
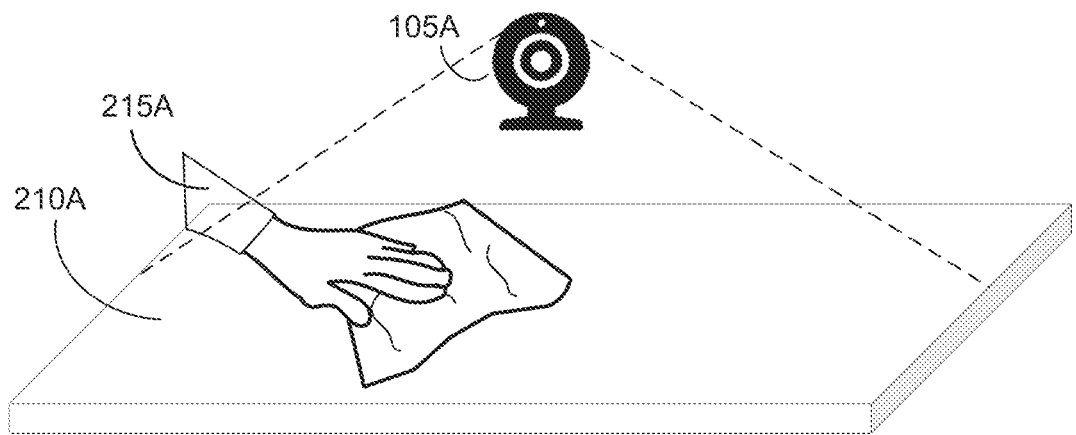
FIGS. 2A-2B are example illustrations of cameras for capturing video streams for use in monitoring and providing feedback for surface cleaning by a cleaning wizard, in accordance with an embodiment.

FIG. 2A is an example illustration of a camera 105A externally positioned to capture a video stream for an item of medical equipment 210A. In an embodiment, the camera 105A is positioned to capture a video stream including at least a surface of an item of medical equipment 210A. In another embodiment, the camera 105A is positioned to capture a video stream including a surface on which items of medical equipment are positioned for cleaning (e.g., the camera is positioned to capture a video stream of a table on which a stethoscope is placed for cleaning purposes). When an operator 215A performs a wiping motion with a cloth across a surface of the item of medical equipment 210A within the video stream captured by the camera 105A, the cleaning wizard 150 initiates a cleaning protocol for the item of medical equipment.

In an embodiment, because external cameras 105A may be moved or positioned incorrectly relative to an item of medical equipment, the cleaning wizard 150 initiates a check for the position of the camera 105A to ensure that the captured video stream accurately represents the cleaning attempt. Thus, in such an embodiment, when a cleaning protocol is initiated, the cleaning wizard 150 may determine a position of the item of medical equipment in the video stream relative to the camera 105A. Responsive to the item of medical equipment 210A being positioned outside of a threshold distance relative to the camera, e.g., too far away or too close to the camera 105A for an accurate analysis of the cleaning attempt to be performed, the cleaning wizard 150 may transmit a notification to the operator to reposition the item of medical equipment. While the cleaning protocol is performed, the cleaning wizard 150 may additionally perform periodic checks for the position of the camera 105A to ensure that the video stream is not occluded, e.g., by an operator or by other items or objects, and that the camera is not moved during the cleaning protocol. Responsive to detecting occlusion for a greater than threshold amount of time or a change in position, the cleaning wizard 150 transmits a notification to the operator to take corrective action.

Figure 2B:
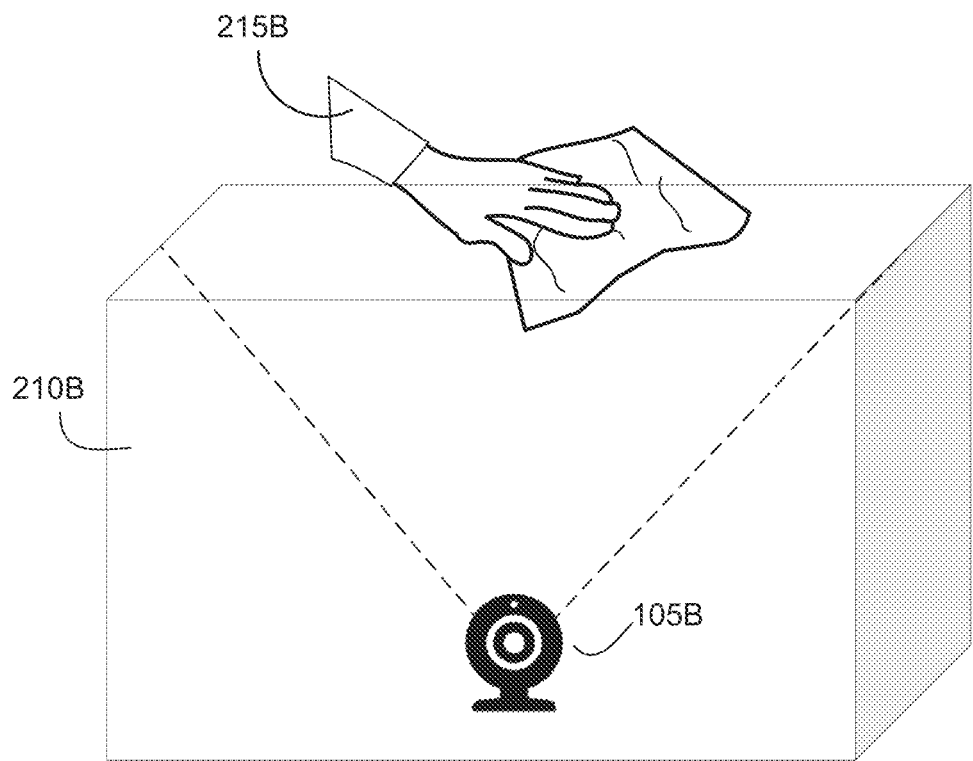

FIG. 2B is an example illustration of a camera 105B mounted to or in an item of medical equipment 210B. In the example of FIG. 2B, the camera 105B is mounted internally to the item of medical equipment 210B and captures a video stream of a surface of the item of medical equipment, e.g., through a transparent or semi-transparent panel, such that when an operator 215B performs a wiping motion with a cloth across the surface of the item of medical equipment, the camera 105B captures the wiping motion on the video stream. For example, the medical equipment may be a retinal camera, where a user places his forehead and chin on the medical equipment and gazes into a glass screen. The retinal camera, or another internal camera, may have the chinrest, the forehead rest, and the glass screen all partially or fully within its view, and may monitor the cleaning protocol without a need for an external camera. In other examples, the camera 105B may be mounted to an external surface or component of the item of medical equipment 210B and may be positioned, attached, or removed by an operator of the item of medical equipment. In another example, the camera 105B may capture a video stream for a cleaning attempt of a component of the camera, e.g., of the lens.

In some embodiments, multiple cameras, including one or more external cameras 105A and one or more internal cameras 105B, are used to capture video streams of medical equipment in order to ensure that the video streams provide a comprehensive view of the medical equipment. For example, a retinal camera having an internal camera 105B may have a partially obscured view of the chinrest and forehead rest, which must be correctly cleaned in addition to a lens of the retinal camera itself. One or more external cameras 105A are positioned to capture blind spots of the internal camera 105B. The video streams of the internal camera 105B and the one or more external cameras 105A are transmitted to the cleaning wizard 150. In an embodiment, video streams are logically stitched for processing by the cleaning wizard 150.

Figure 3:
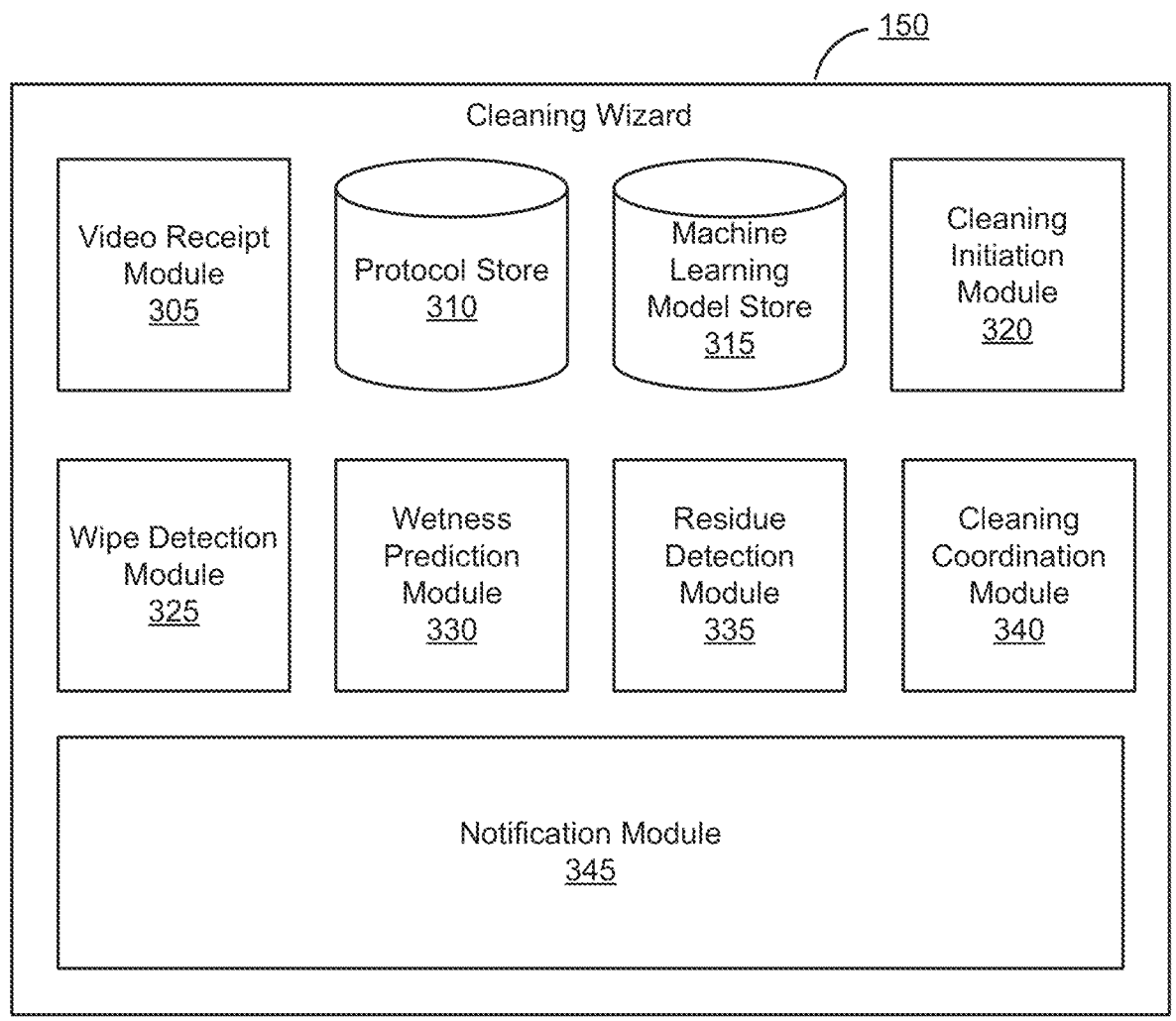
FIG. 3 is a block diagram of an architecture of the cleaning wizard, in accordance with an embodiment.

FIG. 3 is a block diagram of an architecture of the cleaning wizard 150, in accordance with an embodiment. The cleaning wizard 150 shown in FIG. 3 includes a video receipt module 305, a protocol store 310, a machine learning model store 315, a cleaning initiation module 320, a wipe detection module 325, a wetness prediction module 330, a residue detection module 335, a cleaning coordination module 340 and a notification module 345. In other embodiments, the cleaning wizard 150 may include additional, fewer, or different components for various applications. Conventional components such as network interfaces, security functions, load balancers, failover servers, management and network operations consoles, and the like are not shown so as to not obscure the details of the system architecture.

The video receipt module 305 receives video streams from a camera 105. In an embodiment, the video streams are received continuously, periodically, or at some other programmed intervals or regularity. Additionally, or alternatively, the video streams may be initiated by an operator, e.g., at the start of a work day, prior to beginning a cleaning protocol. In an embodiment, the video receipt module 305 transmits sets of frames of the received video stream to the cleaning initiation module 320, the wipe detection module 325, the wetness prediction module 330, and the residue detection module 335. Alternatively, or additionally, video receipt model 305 may store the frames to shared memory accessible by the other modules of cleaning wizard 150, from which those modules may access the frames. In an embodiment, the video stream module 305 receives instructions for storing and/or transmitting the video streams from the cleaning coordination module 340.

The protocol store 310 stores and maintains information describing cleaning protocols. Generally, cleaning protocols specify one or more required values or deficiency values for one or more aspects of a cleaning attempt that must be met in order for the cleaning attempt with a given cleaning agent to be successful for a given item of medical equipment, e.g., to meet CDC guidelines or manufacturer instructions for the cleaning agent. A required value represents a minimum or maximum value required to successfully meet criteria for the cleaning protocol. A deficiency value represents a minimum or maximum value at which a cleaning protocol is failed. In some embodiments, a cleaning protocol may specify a range of acceptable values for one or more aspects of a cleaning protocol, or may specify a threshold value at which a cleaning attempt has not yet failed but requires corrective action. Cleaning protocols may specify, for example, a type, amount, or concentration of cleaning agent to be used for an item of medical equipment; a required wetness for a surface of the item of medical equipment; a duration of time for wiping or for maintaining a surface wetness; rinsing of the surface; a required drying of the surface prior to contacting human skin; and the like.

The machine learning model store 315 stores one or more models trained to output information describing meets criteria of a cleaning protocol. In an embodiment, the one or more models are trained to detect whether cleaning attempts meet criteria of cleaning protocols using positive and negative training samples. Positive training samples may be, for example, video data or frames approved by the CDC, cleaning agent manufacturers, or medical professionals as best practice for cleaning of medical equipment. Negative training samples may be, for example, video data or frames of movement near an item of medical equipment without cleaning the item of medical equipment, incorrect cleaning of the item of medical equipment, and the like. Positive and negative training samples are labeled to identify clips, e.g., as correct cleaning attempts, incorrect cleaning attempts, or not attempted. The one or more models may be trained on, for example, different cleaning agents having different manufacturer instructions, different items of medical equipment having different surfaces, and the like. Particular values of cleaning protocols, such as threshold values for triggering notifications to operators, may be tuned by models or may be manually established.

The cleaning initiation module 320 applies a proposal network to sets of frames from video streams to determine when cleaning protocols are initiated for items of medical equipment. In an embodiment, the proposal network is a machine learned model that is trained to receive sets of frames from video streams as data and to output whether the sets of frames correspond to activity that initiates a cleaning protocol for an item of medical equipment. For example, the proposal network is trained to output that a set of frames corresponds to a cleaning protocol being initiated if the set of frames includes an operator wiping a surface of the item of medical equipment with a cloth or wipe. In another example, the proposal is trained to output that a set of frames corresponds to a cleaning protocol being initiated if the set of frames includes an operator spraying or applying a cleaning agent to a surface of the item of medical equipment.

In an embodiment, the cleaning initiation module 320 applies the proposal network to a sampled frame or subset of frames of the video stream. For example, the cleaning initiation module 320 applies the proposal network to every tenth frame received by the cleaning wizard 150 from the camera 105. Responsive to a cleaning attempt being detected by the cleaning initiation module 320, the cleaning initiation module 320 transmits a set of frames corresponding to a timeframe around the sampled frame or subset of frames to the wipe detection module 325. In an embodiment, the proposal network is a convolutional neural network. In other embodiments, other methods of machine learning may be used.

In an embodiment, the proposal network is a lightweight network used prior to heavy processing performed downstream. Use of the proposal network reduces processing power required by the cleaning wizard 150 when cleaning attempts are not being made. Because the proposal network is run periodically on individual frames or short sets of frames, and as such does not require a large amount of video data processing, the cleaning wizard 150 is able to efficiently identify when a cleaning protocol is initiated by operators of medical equipment without the need for high amounts of computational resources, battery usage, and the like. Where the proposal network outputs that a cleaning protocol is initiated, the cleaning wizard 150 may apply one or more heavyweight networks to confirm that the cleaning protocol is initiated. As such, use of the proposal network prior to heavy processing improves overall efficiency of the cleaning wizard 150 while nonetheless employing a robust network to eliminate the possibility of false positives triggering unneeded cleaning protocol cycles.

Responsive to receiving a set of frames from the cleaning initiation module 320, the wipe detection module 325 applies a wipe detector model to sets of frames from video streams to determine whether cleaning agent has been correctly applied. While "wiping" is a prevalent example throughout this disclosure, this is merely exemplary; any act of cleaning a surface may be used in place of "wiping." For example, wipe detection module 325 may be used to detect, rather than a wiping motion, a rinsing motion, a spraying motion, and so on. In such cases, the term "wipe detection module" is not intended to require a detection of "wiping", and can be used to detect whatever corresponding cleaning mechanism is relevant.

Correct application of a cleaning agent may include spatial and temporal parameters, such as whether the cleaning agent is applied to a sufficient area of the surface of the item of medical equipment and/or whether the cleaning agent is applied within a threshold amount of time. In alternative or additional embodiments, the wipe detection module 325 is used to detect any surface cleaning activity, including alternative methods of applying cleaning agent to a surface. For example, the wipe detection module 325 may detect spraying of a cleaning agent via a spray bottle and/or rinsing a surface with a cleaning agent, e.g., as a running stream of water or cleaning liquid applied to a surface of the item of medical equipment.

In an embodiment, the wipe detector model is trained using positive and negative training samples. Training samples may include video clips including various methods for surface cleaning, including wiping a surface with a cloth, rinsing of the surface, spraying cleaning agent on a surface, and the like. Training samples may be, for example, video clips released by the CDC or by manufacturers of the cleaning agent and labeled, e.g., as correct application of the cleaning agent, incorrect application of the cleaning agent, and nonapplication of the cleaning agent. Training samples may also be generated by skilled users intentionally generating examples with the various labels, or skilled labelers labeling video clips from real cleaning attempts. Additionally, these clips can be collected while the cleaning wizard 150 is in operation and used for ongoing improvements. In an embodiment, the wipe detector model is a three-dimensional convolutional neural network. In other embodiments, other methods of machine learning may be used.

For example, the wipe detector model is trained to receive a set of video frames and a cleaning protocol as input and to output a binary value representing whether the cleaning agent is correctly applied to the item of medical equipment. In another example, the wipe detector model is trained to output a numeric value representing a probability of whether the cleaning agent is correctly applied. Some cleaning protocols do not require application of a cleaning agent (e.g., a rinsing protocol where only water is required); in such cleaning protocols, the wipe detector model may be trained to detect whether the appropriate action has been taken (e.g., the frames reflect that a rinsing has begun). The wipe detection module 325 compares the output probability of the wipe detector model to a threshold probability to determine whether the cleaning agent is correctly applied. In another example, the wipe detector model is trained to output one or more flags representing aspects of the cleaning protocol, e.g., where a flag represents whether cleaning agent is applied to a sufficient area of the item of medical equipment, a flag represents whether cleaning agent is applied within a threshold amount of time, and/or one or more flags representing correct application of the cleaning agent to portions of the item of the medical equipment.

The wipe detection module 325 transmits a notification to the cleaning coordination module 340 responsive to an output by the wipe detector model, including information describing whether the cleaning agent has been correctly applied. Responsive to the wipe detector model outputting that the cleaning agent has been incorrectly applied (or, where wiping or cleaning agent application is not at issue, responsive to detecting that whatever activity was required was done improperly), the wipe detection module 325 may reinitiate the cleaning attempt or may receive sets of frames as additional input to the wipe detector model. For example, if a cleaning attempt fails due to an operator failing to apply cleaning agent to a portion of a surface of the item of medical equipment, the operator may be instructed to apply cleaning agent to the portion rather than restarting the cleaning attempt. The wipe detection module 325 inputs a set of frames from the video stream of the operator applying cleaning agent to the portion in addition to the initial set of frames into the wipe detector model. In another example, if a cleaning attempt fails due to an operator failing to apply sufficient cleaning agent within a timeframe, the operator may be instructed to restart the cleaning attempt. The wipe detection module 325 inputs a set of frames from the video stream of the operator restarting the cleaning attempt into the wipe detector model without the initial set of frames.

The wetness prediction module 330 applies a wetness predictor model to sets of frames from video streams to determine whether sufficient wetness is maintained for surfaces of items of medical equipment during cleaning attempts. For cleaning agents to disinfect a surface sufficiently to prevent the spread of infection, cleaning agents are frequently associated with manufacturer instructions to maintain a threshold wetness of a surface for a period of time. For example, a surface may need to remain wet for three minutes in order for the cleaning agent to disinfect the surface.

In an embodiment, the wetness predictor model is trained using training samples. Training samples may be, for example, frames of video data or images including a hard surface. The training samples are associated with labels identifying the hard surfaces as being sufficiently wet, insufficiently wet, nearly dry, or dry. When frames of video data are labeled, the label of intermediary frames may be interpolated from the already labeled frames. For example, if the surface is wet in frame 1 and in frame 10, frames 2 through 9 can be assumed wet. In other examples, additional, fewer, or different labels may be used. In some examples, portions of surfaces in the training samples may be labeled individually, such that a first portion may be identified as "sufficiently wet," and a second portion may be identified as "dry." In some embodiments, during training on the training samples, the output pixel map may require a smoothness regulation across spatial and time dimensions. This smoothness regulation may take the form of minimizing the derivative of the pixel map. This regulation term would be added with a coefficient to the standard neural network loss.

In an embodiment, the wetness predictor model is a recurrent convolutional neural network. The wetness predictor model receives as input a set of video frames and a cleaning protocol and outputs a pixel map, wherein a per-pixel wetness value is generated for each timestamp of the set of frames. In an example, the wetness predictor model applies a smoothness operation to the set of frames from the video stream to reduce the impact of single pixel errors. In another example, frames are downsized such that each pixel of the output pixel map represents a region of the set of frames, e.g., an initial frame of 10,000×10,000 pixels is downsized and a pixel map is generated at 512×512 pixels. In other embodiments, other methods of machine learning may be used, and other qualitative or quantitative representations of surface wetness may be used.

The wetness prediction module 330 determines, based on the pixel map, an overall wetness value of the surface. In some embodiments, the wetness prediction module 330 applies one or more classifiers trained to receive a pixel map and a cleaning protocol as input and to output a value representing whether pixels of the pixel map individually conform to required values (e.g., wetness values) of the cleaning protocol. In some embodiments, the value may be a binary representation of whether pixels of the pixel map conform to the required values of the cleaning protocol. In other embodiments, the value may be a numeric value representing a percentage of pixels of the pixel map conforming to the required values of the cleaning protocol, or a probability of the pixels of the pixel map individually conforming to required values of the cleaning protocol. In other embodiments, the value may be a numeric value representing an average or minimum wetness of the surface of the medical equipment. The one or more classifiers may be stored in the machine learning model store 315. The wetness prediction module 330 determines, based on the outputs of the one or more classifiers, whether an overall wetness of the surface of the medical equipment meets the criteria of the cleaning protocol.

In other embodiments, the wetness prediction module 330 determines and evaluates a minimum value of the pixel map to ensure that the minimum value of the pixel map is above a specified threshold of the cleaning protocol throughout a required duration of time. The wetness prediction module 330 evaluates a pixel map corresponding to a current frame of the video stream and one or more pixel maps corresponding to one or more previous frames of the video stream, such that the wetness prediction module 330 may alert the cleaning coordination module 340 when the wetness value decreases over time to approach the threshold value.

The residue detection module 335 applies a residue detector model to sets of frames from video streams to determine whether residue on a surface of an item of medical equipment increases or decreases by a sufficient amount during cleaning protocols. In some embodiments, the residue detector model is an alternative to or an addition to the wetness predictor model, in that wetness or droplets of cleaning agent on a surface may be represented as residue. Residue may additionally include, for example, dust or dirt particles, other liquids, and the like.

In an embodiment, the residue detector model is a recurrent convolutional neural network that outputs a pixel map representing a per-pixel amount of residue on a surface of the item of medical equipment. In some examples, the residue detector model outputs one or more pixel maps representing kinds of residue, e.g., a pixel map representing liquid residue on a surface and a pixel map representing dust particles on a surface, wherein the pixel map representing liquid residue on a surface is evaluated to a different threshold or criteria by the residue detection module 335 than the pixel map representing dust particles on the same surface.

The cleaning coordination module 340 receives information describing outputs of machine learning models from the wipe detection module 325, the wetness prediction module 330, and the residue detection module 335 and determines signals based on the received information. The cleaning coordination module 340 monitors outputs from the machine learned models and, responsive to at least one monitored output being within a threshold range of a deficiency value (e.g., a wetness value 0.3 approaching a deficiency value 0.2), the cleaning coordination module signals the notification module 345 to notify an operator to correct the deficiency. Responsive to at least one monitored output failing to meet the deficiency value (e.g., a wetness value 0.1 being less than a deficiency value 0.2 due to an operator failing to reapply the cleaning agent in time), the cleaning coordination module 340 signals the notification module 345 to notify an operator to restart the cleaning protocol, and signals the wipe detection module 325 to restart the cleaning protocol. Responsive to all monitored outputs meeting criteria of the cleaning protocol, the cleaning coordination module 340 signals the notification module 345 to notify an operator that the cleaning protocol is complete.

In some embodiments, the cleaning coordination module 340 additionally identifies a cleaning protocol for use in a cleaning attempt. Because cleaning protocols may differ between cleaning agents and items of medical equipment, the cleaning coordination module 340 determines, responsive to initiation of a cleaning attempt by an operator, at least one of a type of cleaning agent being used during the cleaning attempt and an item of medical equipment being cleaned. For example, the cleaning coordination module 340 may apply a model trained to identify a type of cleaning agent and an item of medical equipment from visual data, e.g., based on a brand name or label appearing in the video stream, an application method of the cleaning agent, a spatial shape of the medical equipment, and the like. In other embodiments, the cleaning coordination module 340 receives, as input from an operator, information specifying a type of cleaning agent and an item of medical equipment being cleaned. Based on the information, the cleaning coordination module 340 accesses the protocol store 310 and selects a cleaning protocol to be applied to the cleaning attempt. In an embodiment, the cleaning agent may simply be water (e.g., as called for in a rinsing protocol).

The notification module 345 transmits notifications to one or more client devices 110 to provide feedback during cleaning attempts of items of medical equipment. The notification module 345 communicates with a client device 110 of an operator performing a cleaning protocol via the network 115. Responsive to a signal from the cleaning coordination module 340, the notification module 345 provides text or image notifications to the operator to perform corrective actions during the cleaning attempt, to restart the cleaning attempt, or upon successful completion of the cleaning protocol. Example notifications are further discussed in conjunction with FIG. 5.

In alternative embodiments, one or more modules may be omitted to streamline the functionality of the cleaning wizard 150. For example, in one alternative embodiment, the cleaning initiation module 320 and the proposal network are omitted. In this embodiment, the wipe detection module 325 may be prompted to run responsive to the cleaning coordination module 340 signaling that an operator is being prompted to reapply the cleaning agent. Alternatively, the wipe detection module 325 is prompted to run throughout the cleaning protocol, e.g., responsive to the cleaning wizard 150 being initiated or turned on.

In another alternative embodiment, the wipe detection module 325 and the wipe detector model are omitted. In this embodiment, the cleaning initiation module 320 applies the proposal network to determine when a cleaning attempt is initiated, and the wetness predictor model 330 applies a wetness predictor model to determine when portions of a surface become too dry or did not have the cleaning agent appropriately applied in the initial application. This embodiment may also be used where a non-wipe method such as rinsing is used to apply the cleaning agent.

In another alternative embodiment, the wetness prediction model 330 and the wetness predictor model are omitted. In this embodiment, the cleaning coordination module 340 signals the notification module 345 to notify an operator to reapply cleaning agent at periodic intervals after an initial application of the cleaning agent. The periodic intervals are timed such that, for a sufficient application of the cleaning agent, a wetness value of the surface of the item of medical equipment is maintained. If sufficient application is not detected by the wipe detection module 340 during each interval (e.g., an interval is missed or a portion of the surface is missed), the cleaning coordination module 340 signals the notification module 345 to notify the operator that the cleaning protocol has failed and must be restarted.

Figure 4:
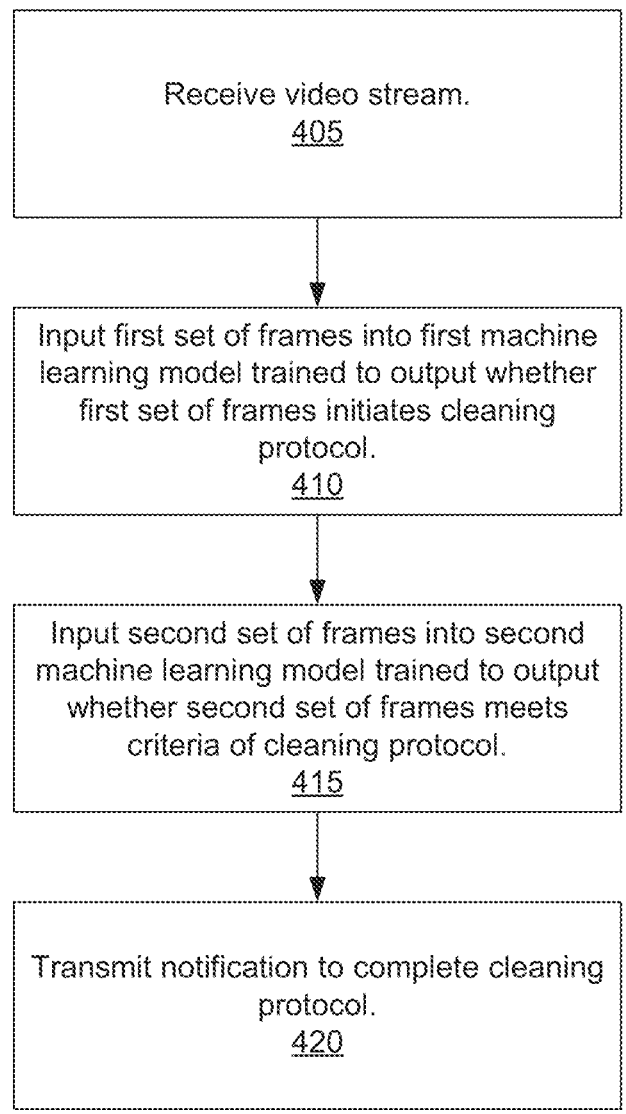
FIG. 4 is an example flowchart of a method for monitoring and providing feedback for surface cleaning of a medical surface, in accordance with an embodiment.

FIG. 4 is an example flowchart of a method for monitoring and providing feedback for surface cleaning of a medical surface, in accordance with an embodiment. The steps of FIG. 4 may be performed by the cleaning wizard 150 as described below. Some or all of the steps may be performed by other modules in other embodiments. In addition, other embodiments may include different and/or additional steps and the steps may be performed in different orders.

The video receipt module 305 of the cleaning wizard 150 receives 405 a video stream. The cleaning initiation module 320 inputs 410 a first set of frames of the video stream into a first machine learning model. The first machine learning model is stored in the machine learning model store 315 and is trained to output whether the first set of frames corresponds to activity that initiates a cleaning protocol for an item of medical equipment. One or more cleaning protocols are stored by the cleaning wizard 150 in the protocol store 310, and may be accessed by the cleaning initiation module 320. In an example, the first machine learning model is trained to output that the cleaning protocol is initiated responsive to detecting a wiping motion made with a cloth across a surface of the item of medical equipment in the first set of frames. In another example, the first machine learning model is trained to output that the cleaning protocol is initiated responsive to detecting a cleaning agent is sprayed upon a surface of the item of medical equipment in the first set of frames.

Responsive to the cleaning protocol being initiated, the cleaning wizard 150 inputs 415 a second set of frames of the video stream into a second machine learning model stored in the machine learning model store 315. The second machine learning model is trained to output whether the second set of frames meets criteria of the cleaning protocol. The cleaning protocol may specify one or more deficiency values for aspects of a cleaning attempt at which a cleaning attempt fails and/or required values for aspects of a cleaning attempt that must be met for a cleaning attempt to be successful. A cleaning coordination module 340 of the cleaning wizard may signal one or more modules to apply one or more machine learning models based on the specified aspects of the cleaning attempt. For example, the wetness prediction module 330 inputs the second set of frames into a machine learning model trained to output a representation of surface wetness of the item of medical equipment during the cleaning attempt. Alternatively, or additionally, the wipe detection module 325 inputs the second set of frames into a machine learning model trained to output whether cleaning agent is correctly applied to the item of medical equipment. Alternatively, or additionally, the residue detection module 335 inputs the second set of frames into a machine learning model trained to output a representation of residue on one or more surfaces of the item of medical equipment during the cleaning attempt.

In an embodiment, the second machine learning model may additionally or alternatively comprise one or more classifiers, the one or more classifiers trained to output whether aspects of the cleaning attempt captured in the second set of frames conforms to criteria of the cleaning protocol. For example, the second machine learning model determines whether criteria such as surface wetness, surface residue, and surface coverage by a spray or wipe are kept in the correct range for the duration of the second set of frames. The one or more classifiers output, for each aspect of the cleaning protocol, whether pixels of the pixel map conform to the required values of the cleaning protocol.

Responsive to an output of the second machine learning model being within a threshold range of a deficiency value of the cleaning protocol, e.g., a surface having a value of surface wetness at 0.3 for a deficiency value of 0.2, the cleaning coordination module 340 of the cleaning wizard 150 signals the notification module 345 to transmit a notification to the operator to correct the deficiency. For example, the notification may instruct the operator to reapply cleaning agent to at least a portion of the surface of the item of medical equipment. Responsive to an output of the second machine learning model failing to meet a deficiency value of the cleaning protocol, e.g., a surface having a value of surface wetness of 0.1 for a deficiency value of 0.2, the cleaning coordination module 340 signals the notification module 345 to transmit a notification to the operator to restart the cleaning protocol.

Responsive to an output of the second machine learning model meeting the criteria of the cleaning protocol, the cleaning coordination module 340 signals the notification module 345 to transmit 420 a notification to the operator that the cleaning protocol has been successfully completed.

Figure 5:
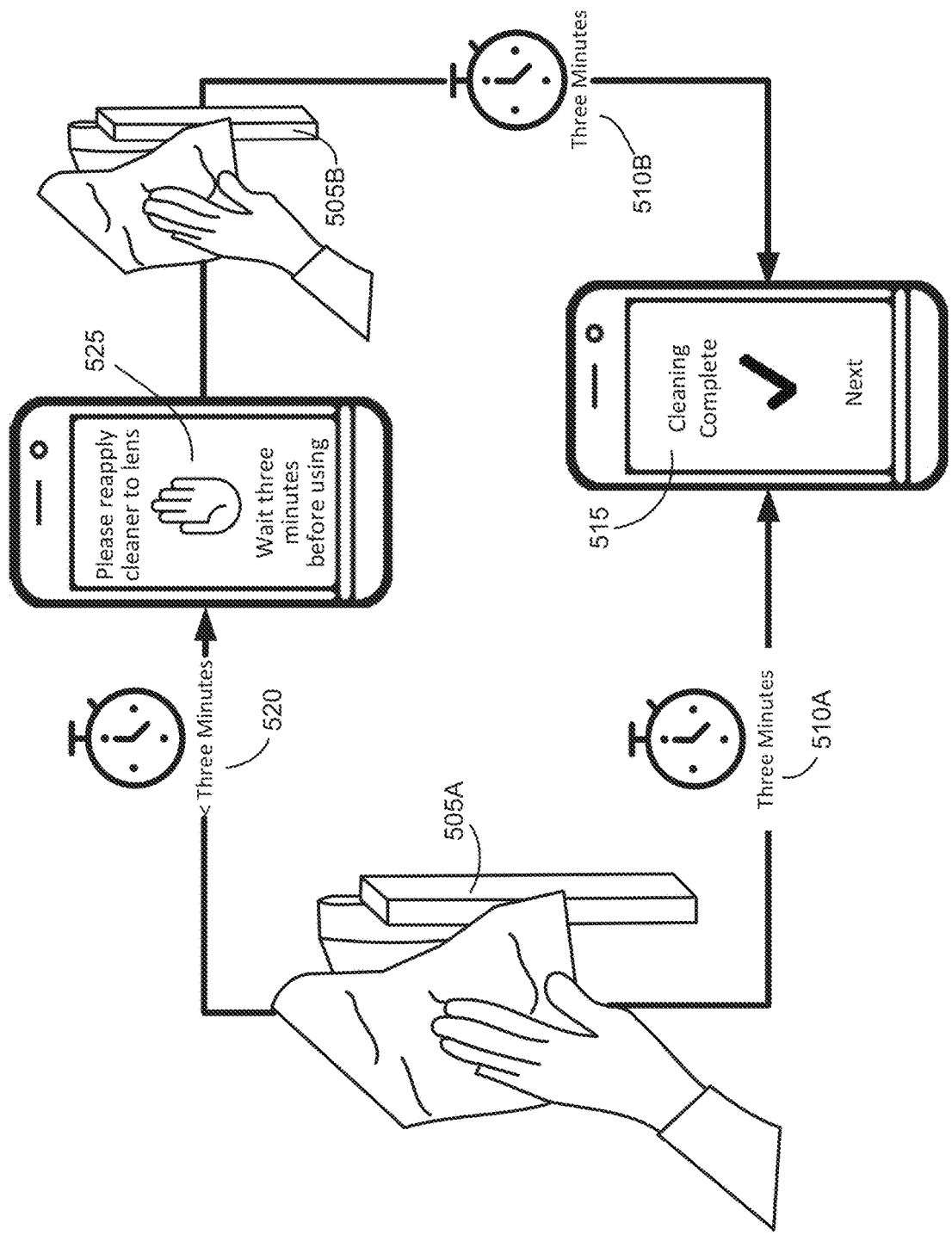
FIG. 5 is an example illustration of a method for monitoring and providing feedback for surface cleaning of a medical surface, in accordance with an embodiment.

FIG. 5 is an example illustration of a method for monitoring and providing feedback for surface cleaning of a medical surface, in accordance with an embodiment. A camera 105 captures a video stream of an item of medical equipment and transmits the video stream to a cleaning wizard 150. An operator of the item of medical equipment initiates a cleaning protocol 505A by performing a wipe of a surface of the item of medical equipment with a cloth. Responsive to determining that the cleaning protocol has been initiated, the cleaning wizard 150 determines required values for the cleaning protocol to be successfully completed. In the example of FIG. 5, a required value for the cleaning protocol specifies that a surface of the item of medical equipment maintains surface wetness for three minutes in order for the surface to be sufficiently cleaned. In other examples, other required values and other aspects of the cleaning protocol may be specified.

Responsive to the surface of the item of medical equipment maintaining surface wetness for the required three minutes 510A, the cleaning wizard completes the cleaning protocol and transmits a notification 515 to a client device 110 of the operator that the cleaning protocol is complete, e.g., "Cleaning Complete" and one or more visual elements indicating successful completion of the cleaning protocol.

Responsive to the cleaning wizard 150 determining that the surface of the item of medical equipment has failed to maintain surface wetness for three minutes 520, the cleaning wizard transmits a notification 525 to a client device 110 of the operator. The notification 525 specifies instructions for the operator to restart the cleaning protocol, e.g., "Please reapply cleaner to lens. Wait three minutes before using." The operator of the item of medical equipment reinitiates the cleaning protocol 505B by reapplying cleanser to the surface of the item of medical equipment. Responsive to the cleaning wizard 150 determining that the cleaning protocol has been reinitiated 505B, the cleaning wizard monitors the cleaning attempt to ensure that surface wetness is maintained for the required three minutes. Upon surface wetness being maintained for the required three minutes 510B, the cleaning wizard 150 completes the cleaning protocol and transmits a notification 515 to a client device 110 of the operator that the cleaning protocol is complete.

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A method comprising:
    receiving a video stream;
    inputting a first set of frames of the video stream into a first machine learning model, the first machine learning model trained to output whether the first set of frames corresponds to activity that initiates a cleaning protocol for an item of medical equipment;
    responsive to receiving output that the first set of frames corresponds to activity that initiates the cleaning protocol, inputting a second set of frames from the video stream into a second machine learning model, the second machine learning model trained to output a pixel map, the pixel map representing one or more aspects of the cleaning protocol based on the second set of frames;
    inputting the pixel map into one or more classifiers;
    receiving, as output from each of the one or more classifiers, whether pixels of the pixel map conform to required values of the cleaning protocol; and
    responsive to the pixels of the pixel map conforming to the required values of the cleaning protocol, determining that the second set of frames meets criteria of the cleaning protocol; and
    responsive to the second set of frames meeting the criteria of the cleaning protocol, transmitting a notification to an operator that the cleaning protocol is complete.

2. The method of claim 1, wherein the criteria of the cleaning protocol includes a deficiency value for an aspect of the cleaning protocol.

3. The method of claim 2, wherein the second machine learning model generates an output for each frame of the second set of frames, and wherein the method further comprises:
    analyzing a given output of the second machine learning model corresponding to a given frame of the second set of frames; and responsive to the given output being within a threshold range of the deficiency value, transmitting a notification to the operator to correct a deficiency.

4. The method of claim 3, further comprising:
monitoring outputs of the second machine learning model corresponding to frames following the given frame; and
responsive to at least one of the monitored outputs failing to meet the deficiency value, transmitting a notification to the operator to restart the cleaning protocol.

5. The method of claim 1, wherein the first machine learning model is a proposal network.

6. The method of claim 1, wherein the first machine learning model is trained to output that the cleaning protocol is initiated responsive to detecting a wiping motion made with a cloth across a surface of the item of medical equipment in the first set of frames.

7. The method of claim 1, further comprising:
further responsive to receiving output that the first set of frames corresponds to activity that initiates the cleaning protocol, determining a position of the item of medical equipment in the video stream relative to a camera capturing the video stream; and
responsive to the item of medical equipment being positioned outside of a threshold distance relative to the camera, transmitting a notification to the operator to reposition the item of medical equipment.

8. The method of claim 1, wherein the video stream is captured by a camera mounted to or in the item of medical equipment.

9. The method of claim 1, wherein the cleaning protocol includes a required value of wetness of a surface of the item of medical equipment.

10. The method of claim 1, wherein initiating the cleaning protocol for the item of medical equipment further comprises:
determining a type of cleaning agent used during the cleaning protocol, based at least in part on the first set of frames; and
adjusting the criteria of the cleaning protocol based on the determined type of cleaning agent.

11. A non-transitory computer-readable storage medium comprising memory with instructions encoded thereon, the instructions executable by one or more processors to perform operations, the instructions comprising instructions to:
receive a video stream;
input a first set of frames of the video stream into a first machine learning model, the first machine learning model trained to output whether the first set of frames corresponds to activity that initiates a cleaning protocol for an item of medical equipment;
responsive to receiving output that the first set of frames corresponds to activity that initiates the cleaning protocol, input a second set of frames from the video stream into a second machine learning model, the second machine learning model trained to output a pixel map, the pixel map representing one or more aspects of the cleaning protocol based on the second set of frames;
input the pixel map into one or more classifiers;
receive, as output from each of the one or more classifiers, whether pixels of the pixel map conform to required values of the cleaning protocol; and
responsive to the pixels of the pixel map conforming to the required values of the cleaning protocol, determine that the second set of frames meets criteria of the cleaning protocol; and
responsive to the second set of frames meeting the criteria of the cleaning protocol, transmit a notification to an operator that the cleaning protocol is complete.

12. The non-transitory computer-readable storage medium of claim 11, wherein the criteria of the cleaning protocol includes a deficiency value for an aspect of the cleaning protocol.

13. The non-transitory computer-readable storage medium of claim 12, wherein the second machine learning model generates an output for each frame of the second set of frames, and wherein the instructions further comprise instructions to:
analyze a given output of the second machine learning model corresponding to a given frame of the second set of frames; and
responsive to the given output being within a threshold range of the deficiency value, transmit a notification to the operator to correct a deficiency.

14. The non-transitory computer-readable storage medium of claim 13, wherein the instructions further comprise instructions to:
monitor outputs of the second machine learning model corresponding to frames following the given frame; and
responsive to at least one of the monitored outputs failing to meet the deficiency value, transmit a notification to the operator to restart the cleaning protocol.

15. The non-transitory computer-readable storage medium of claim 11, wherein the first machine learning model is a proposal network.

16. A system comprising:
memory with instructions encoded thereon; and
one or more processors that, when executing the instructions, are caused to perform operations comprising:
receiving a video stream;
inputting a first set of frames of the video stream into a first machine learning model, the first machine learning model trained to output whether the first set of frames corresponds to activity that initiates a cleaning protocol for an item of medical equipment;
responsive to receiving output that the first set of frames corresponds to activity that initiates the cleaning protocol, inputting a second set of frames from the video stream into a second machine learning model, the second machine learning model trained to output a pixel map, the pixel map representing one or more aspects of the cleaning protocol based on the second set of frames;
inputting the pixel map into one or more classifiers;
receiving, as output from each of the one or more classifiers, whether pixels of the pixel map conform to required values of the cleaning protocol; and
responsive to the pixels of the pixel map conforming to the required values of the cleaning protocol, determining that the second set of frames meets criteria of the cleaning protocol;
responsive to the second set of frames meeting the criteria of the cleaning protocol, transmitting a notification to an operator that the cleaning protocol is complete.

17. The system of claim 16, wherein the criteria of the cleaning protocol includes a deficiency value for an aspect of the cleaning protocol.

18. The system of claim 17, wherein the second machine learning model generates an output for each frame of the second set of frames, and wherein the one or more processors are caused to perform operations further comprising:

analyzing a given output of the second machine learning model corresponding to a given frame of the second set of frames; and responsive to the given output being within a threshold range of the deficiency value, transmitting a notification to the operator to correct a deficiency.

* * * * *